United States Patent [19]

Weber

[11] Plant 4,765

[45] Sep. 8, 1981

[54] CHRYSANTHEMUM PLANT

[75] Inventor: Lawrence A. Weber, Milwaukie, Oreg.

[73] Assignee: Weber's Riverside Greenhouses, Milwaukie, Oreg.

[21] Appl. No.: 75,151

[22] Filed: Sep. 12, 1979

[51] Int. Cl.[3] ..... A01H 5/00

[52] U.S. Cl. ..... Plt./78

[58] Field of Search ..... Plt./78

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant with flat decorative capitulum which is a sport of the cultivar Orange Bowl, being distinguished from the parent cultivar by its golden yellow ray floret color.

1 Drawing Figure

The present invention comprises a new and distinct cultivar of *Chrysanthemum morifolium,* Ramat., hereinafter referred to by the cultivar name of Golden Bowl.

Golden Bowl is a spontaneous mutation of the unpatented cultivar Orange Bowl and was selected to expand the color range of the parental variety.

Golden Bowl was discovered and selected by Lawrence A. Weber on June 29, 1976 as one plant within a flowering block of Orange Bowl in Milwaukie, Oreg. The first act of asexual reproduction of Golden Bowl was accomplished on Sept. 8, 1976 when vegetative cuttings were taken from the initial selection in Milwaukie, Oreg. by Lawrence A. Weber.

Continued asexual reproduction by cuttings for evaluative flowering in conjunction with horticultural examination of selected units initiated Feb. 1, 1978 has demonstrated that the combination of characteristics as herein disclosed for Golden Bowl are firmly fixed and are retained through successive generations of asexual reproduction.

Golden Bowl has not been observed under all possible environmental conditions. The phenotype may vary significantly with variations in environment such as temperature, light intensity and daylength. The following observations, measurements and comparisons describe plants grown in Milwaukie, Oreg. and Salinas, Calif. under environmental conditions which approximate those generally used in commercial practice.

The following traits have been repeatedly observed and are determined to be basic characteristics of Golden Bowl which in combination distinguish this chrysanthemum as a new and distinct cultivar:

(1) decorative capitulum type;

(2) informal incurved capitulum form;

(3) golden yellow ray floret color;

(4) diameter across face of inflorescence ranging from 125 to 150 mm. at maturity;

(5) uniform ten week photoperiodic flowering response to short days;

(6) medium plant height (requiring 1-2 long day weeks prior to pinch and short days, and 1 application 2500 ppm. B-9 Sp 14 to 21 days after pinch to attain a flowered plant height of 30 to 35 cm. when grown as a pinched disbudded pot plant for April through November flowerings in Salinas, Calif.); and (7) spreading branching pattern.

The accompanying color photographic drawing shows typical inflorescence and foliage characteristics of Golden Bowl. Some difficulty was encountered in obtaining accurate color representation, with the photographic rendition being more red and less yellow than the actual ray floret color of Golden Bowl. The color values stated below are, however, correct.

Of the many commercial cultivars known to the present inventors, the most similar in comparison to Golden Bowl is the parental cultivar Orange Bowl. Reference is made to attached Chart A which compares certain characteristics of Golden Bowl with the same characteristics of Orange Bowl. In comparison to Orange Bowl, Golden Bowl has different ray floret color. Other characteristics of Golden Bowl are similar to those same characteristics of Orange Bowl.

In the following description, color references are made to A Limit Color Cascade, published by the Munsell Company, 1972 edition. The color values were determined between 11:30 and 12:00 a.m. on June 1, 1979 under 100 foot-candle light intensity at Salinas, Calif.

Classification:

*Botanical.*—*Chrysanthemum morifolium,* Ramat., cv Golden Bowl.

*Commercial.*—Pinched or single stem disbudded pot plant.

I. INFLORESCENCE

A. Capitulum:

*Form.*—Informal incurve.

*Type.*—Decorative.

*Diameter across face.*—125 to 150 mm.

B. Corolla of ray florets:

*Color (general tonality).*—Dark yellow (25-6).

*Color (abaxial).*—Approximately 26-6 oxidizing with age to 25-6.

*Color (adaxial).*—Approximately 25-5.

C. Reproductive organs:

*Androecium.*—Absent.

*Gynoecium.*—Present ray florets.

II. PLANT

A. General appearance:

*Height.*—Medium (pot mum culture).

*Branching pattern.*—Spreading.

B. Foliage:

*Color (abaxial).*—Approximately 21-14.

*Color (adaxial).*—Approximately 21-14 overlaid with white.

CHART A

COMPARISON OF GOLDEN BOWL AND ORANGE BOWL

| CULTIVAR | RAY FLORET COLOR | DIAMETER ACROSS FACE OF CAPITULUM | PLANT HEIGHT |
|---|---|---|---|
| GOLDEN BOWL | GOLDEN YELLOW | 125 to 150 mm. | medium |
| ORANGE BOWL | ORANGE BRONZE | 125 to 150 mm. | medium |

| CULTIVAR | BRANCHING PATTERN | FLOWERING RESPONSE PERIOD | CAPITULUM FORM AND TYPE |
|---|---|---|---|
| GOLDEN BOWL | spreading | 10 week | informal incurved decorative |
| ORANGE BOWL | spreading | 10 week | informal incurved |

CHART A-continued

COMPARISON OF GOLDEN BOWL AND ORANGE BOWL decorative

COMPARISONS MADE OF PLANTS GROWN IN MILWAUKIE, OREGON AND SALINAS CALIFORNIA AS PINCHED DISBUDDED PLANTS.

I claim:

1. A new and distinct cultivar of *Chrysanthemum morifolium,* Ramat., known by the cultivar name Golden Bowl, as described and illustrated, and particularly characterized as to uniqueness by the combined characteristics of decorative capitulum type; informal incurved form; golden yellow ray floret color; diameter across face of capitulum from 125 to 150 mm. at maturity; uniform ten week flowering response to photoperiodic short-day control; medium plant height, and spreading branching pattern.

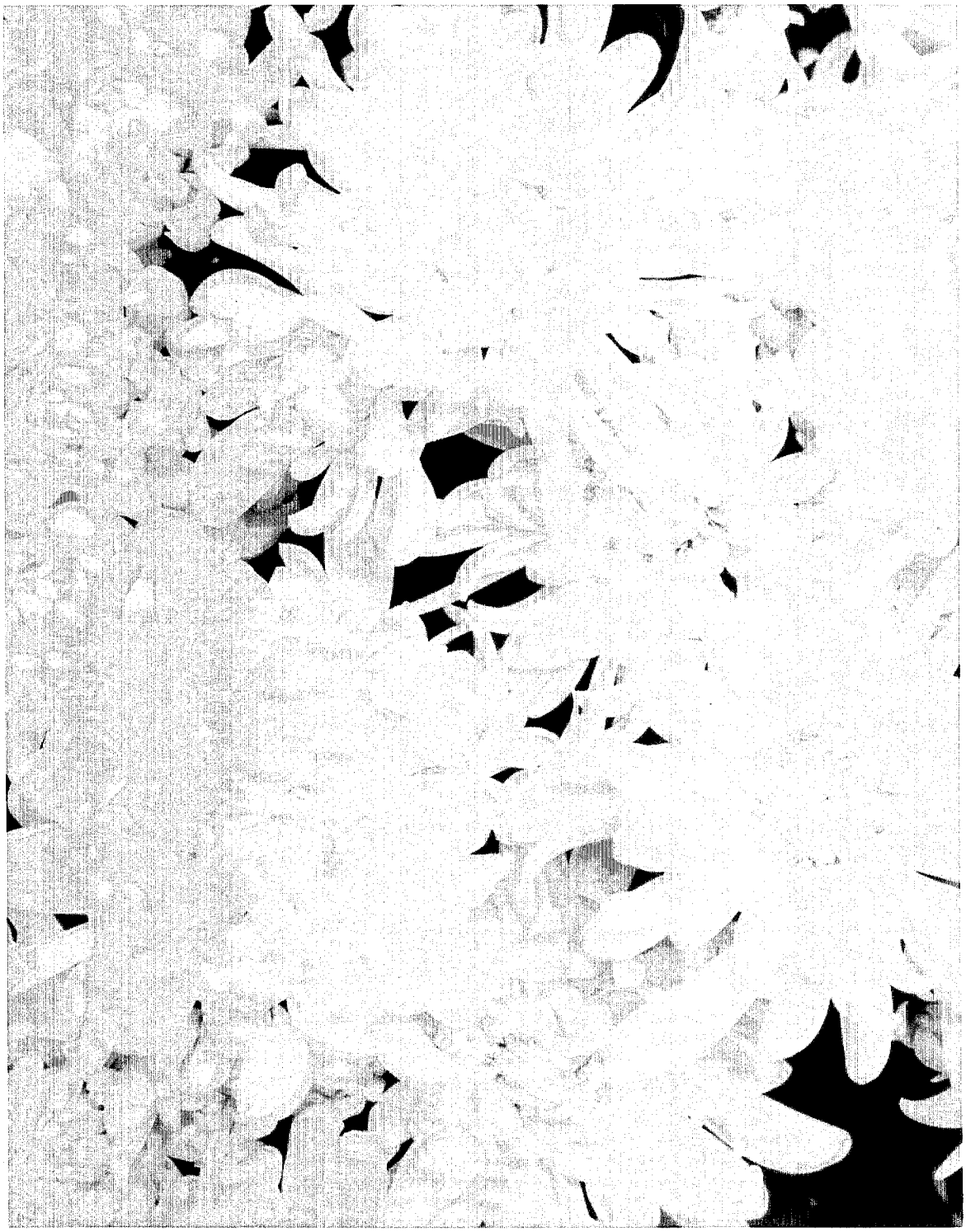

* * * * *